United States Patent [19]

Romeo

[11] Patent Number: 4,876,082

[45] Date of Patent: Oct. 24, 1989

[54] TOOTH-PASTE WITH BRUSHING TIME INDICATOR

[76] Inventor: Roch Romeo, 9, Rue Treilhard, 75008 Paris, France

[21] Appl. No.: 214,222

[22] Filed: Jul. 1, 1988

[30] Foreign Application Priority Data

Jul. 6, 1987 [FR] France .................. 87 09551

[51] Int. Cl.$^4$ ............................... A61K 7/16
[52] U.S. Cl. ............................ 424/7.1; 424/49
[58] Field of Search ................... 424/7.1, 49

[56] References Cited

U.S. PATENT DOCUMENTS

| | | | |
|---|---|---|---|
| 2,470,906 | 5/1949 | Taylor | 424/49 |
| 3,886,265 | 5/1975 | Evers et al. | 424/49 |
| 4,150,106 | 4/1979 | Assal et al. | 424/7.1 |
| 4,223,003 | 9/1980 | Scheller | 424/7.1 |
| 4,229,430 | 10/1980 | Fahim et al. | 424/145 |
| 4,348,378 | 9/1982 | Kusti | 424/49 |
| 4,459,277 | 7/1984 | Kosti | 424/49 |
| 4,568,534 | 2/1986 | Stier et al. | 424/7.1 |

FOREIGN PATENT DOCUMENTS

| | | |
|---|---|---|
| 0218732 | 9/1985 | European Pat. Off. |
| 56-100384 | 8/1981 | Japan ................ 424/7.1 |
| 215518 | 6/1941 | Switzerland. |

OTHER PUBLICATIONS

Chemical Abstracts, vol. 82, No. 8, Apr. 21, 1975, p. 349, Resume No. 103032j, Columbus, Ohio; & JP-A-74 71 151, (Lion Dentrifrice Co., Ltd.), 10-07-1974.

Chemical Abstracts, vol. 107, No. 18, Nov. 2, 1987, Resume No. 161424j, Columbus, Ohio & JP-A-62 89 613, (Kao Corp.), 24-04-1987.

Chemical Abstracts, vol. 104, No. 4, Jan., 1986, p. 290, Resume No. 24979z, Columbus, Ohio & JP-A-60 40 401, (Lion Corp.), Sept. 11, 1987. (The above should not be considered a complete list.)

*Primary Examiner*—Shep K. Rose
*Attorney, Agent, or Firm*—Pollock, Vande Sande & Priddy

[57] ABSTRACT

A tooth-paste comprising an addition of a coloring agent and of a reducing agent for decoloring said tooth paste under the effect of the brushing, characterized in that it is made of a fluorine-based tooth-paste, of the type available in the trade, including methylene blue in a proportion of the order of 500 $\mu$l to 1 ml, in a 1 mg/ml solution, for 5 g of tooth-paste, that is a proportion of the order of 0.125 to 0.250 $\mu$M per gram of tooth-paste, and a reducing agent constituted by sodium ascorbate in powder form which is added at the moment of use.

3 Claims, No Drawings

TOOTH-PASTE WITH BRUSHING TIME INDICATOR

FIELD AND BACKGROUND OF THE INVENTION

The present invention relates to improvements to tooth-pastes.

It is well known that, in dental hygiene, the brushing time of the teeth is a particularly important factor. This brushing time is generally difficult to appreciate and, until now, no efficient and practical solution has been proposed for solving this problem. Actually, efforts have been made (Chemical Abstracts vol. 82 No 8, Apr. 21, 1975, page 349, Summary No 103032j) to solve this problem by incorporating into the tooth-pasge a natural pigment absorbed by absorbants such as cellulose, so as to obtain an indication relative to the efficient cleaning of the teeth via a modification of color. The same concern is also shown in "Chemical Abstracts vol. 104, No 4, January 1986, page 290, Summary No 24979z" which discloses a tooth-paste composition exhibiting a change of color during the application, which includes a coloring agent and a reducing agent. Experience shows that none of the prior techniques allows, on the one hand, obtaining a good initial coloration of the tooth-paste and, on the other hand, a pure decoloration of the tooth-paste after an efficient brushing time, generally evaluated to about 3 minutes. The present invention aims at providing a new tooth-paste composition allowing the user to know with sufficient precision the minimum brushing time necessary for an efficient brushing.

OBJECTS AND SUMMARY OF THE INVENTION

Consequently, the object of this invention is a tooth-paste comprising an addition of a coloring agent and of a reducing agent for decoloring and tooth-paste under the effect of the brushing, characterized in that it is made of a fluorine-based tooth-paste, of the type available in the trade, including methylene blue in a proportion of the order of 500 $\mu$l to 1 ml, in a 1 mg/l solution, for 5 g of tooth-paste, that is a proportion of the order of 0.125 to 0.250 $\mu$M per grams of tooth-paste, and a reducing agent constituted by sodium ascorbate in powder form which is added at the moment of use.

According to a feature of the present invention, the reducing agent is added to the colored tooth-paste in a proportion of the order of 90 mg for 5 g of tooth-paste.

DETAILED DESCRIPTION OF THE INVENTION

Hereafter is given an example of a non-limiting embodiment of an improved tooth-paste according to the invention. Obviously, this is only an example and any other embodiment and/or variant thereof could also be envisaged without departing from the scope of this invention.

An aqueous solution of 1 mg/ml methylene blue was prepared. To 5 g of flourine-based tooth-paste, presently available in the trade, weighed in a porcelain or pyrex cup, have been mixed 500 $\mu$M or 1 ml of the methylene blue solution, that is 0,125 or 0.250 $\mu$M per gram of tooth-paste. The concentration is chosen so as to obtain a good initial coloration of the tooth-paste.

To the colored tooth-paste has been added, at the moment of use, a reducing agent constituted by sodium ascorbate in powder form, according to a proportion of 90 mg of sodium ascorbate for 5 g of tooth-paste. A pure decoloration of the tooth-paste has been observed after a brushing time of about 3 minutes.

In order to put in practical use the tooth-paste which is the object of the present invention, this tooth-paste is conditioned in a standard tube comprising one or several columns in which is placed the sodium ascorbate, the standard fluorine-based tooth-paste occupying the cylindrical volume available about the sodium ascorbate columns, the tooth-paste plus sodium ascorbate mixture being thus provided at the moment of use by pressing the tube in the usual manner.

Of course, the present invention is not limited to the embodiment hereinabove described and it encompasses all the variants thereof.

I claim:

1. A tooth-paste comprising a coloring agent to produce a colored toothpaste and a reducing agent for decoloring said tooth-paste under the effect of brushing, wherein said tooth-paste is fluorine-based and contains methylene blue in a proportion of 500 $\mu$l to 1 ml, in a 1 mg/ml solution, for 5 grams of tooth-paste and a reducing agent comprising sodium ascorbate in powder form for mixing with the coloring agent at the moment of use.

2. A tooth-paste according to claim 1, wherein said sodium ascorbate is added to the colored tooth-paste at the moment of use in a proportion of the order of 90 mg for 5 grams of tooth-paste.

3. A tooth-paste according to claim 1, wherein said tooth-paste is dispersed within a tube comprising at least one column which contains said sodium ascorbate, the remaining portion of the tube containing tooth-paste, colored with methylene blue, whereby the colored tooth-paste plus reducing agent mixture is provided at the moment of use by pressing the tube.

* * * * *

UNITED STATES PATENT AND TRADEMARK OFFICE
CERTIFICATE OF CORRECTION

PATENT NO. : 4,876,082
DATED : October 24, 1989
INVENTOR(S) : Roch Romeo

It is certified that error appears in the above-identified patent and that said Letters Patent is hereby corrected as shown below:

Column 1, line 18, change "pasge" to --paste--.

Column 2, line 13, change "500µM" to --500µl--.

Column 2, line 14, change "0,125" to --0.125--.

Signed and Sealed this

Twenty-fifth Day of December, 1990

Attest:

HARRY F. MANBECK, JR.

*Attesting Officer*          *Commissioner of Patents and Trademarks*